United States Patent
Peace et al.

(10) Patent No.: US 9,517,316 B2
(45) Date of Patent: Dec. 13, 2016

(54) MULTIPLE-USE AIRWAY MASK

(71) Applicants: Roscoe C Peace, New York, NY (US); Gaspare Leo, Valley Stream, NY (US)

(72) Inventors: Roscoe C Peace, New York, NY (US); Gaspare Leo, Valley Stream, NY (US)

(*) Notice: Subject to any disclaimer, the term of this patent is extended or adjusted under 35 U.S.C. 154(b) by 850 days.

(21) Appl. No.: 13/680,041

(22) Filed: Nov. 17, 2012

(65) Prior Publication Data
US 2013/0125893 A1    May 23, 2013

Related U.S. Application Data

(60) Provisional application No. 61/561,617, filed on Nov. 18, 2011.

(51) Int. Cl.
| | |
|---|---|
| *A61M 16/00* | (2006.01) |
| *A61M 15/00* | (2006.01) |
| *A61M 16/06* | (2006.01) |
| *A61M 16/20* | (2006.01) |
| *A61M 16/04* | (2006.01) |
| *A61M 16/08* | (2006.01) |

(52) U.S. Cl.
CPC ..... *A61M 16/0605* (2014.02); *A61M 16/0078* (2013.01); *A61M 16/0084* (2014.02); *A61M 16/0465* (2013.01); *A61M 16/06* (2013.01); *A61M 16/0816* (2013.01); *A61M 16/20* (2013.01); *A61M 16/0434* (2013.01); *A61M 16/0497* (2013.01); *A61M 16/208* (2013.01)

(58) Field of Classification Search
None
See application file for complete search history.

(56) References Cited

U.S. PATENT DOCUMENTS

| | | | | |
|---|---|---|---|---|
| 4,266,540 | A * | 5/1981 | Panzik et al. | 128/207.13 |
| 5,217,006 | A * | 6/1993 | McCulloch | 128/205.13 |
| 5,628,305 | A * | 5/1997 | Melker | 128/202.29 |
| 5,944,013 | A * | 8/1999 | Burch | 128/205.14 |
| 6,202,646 | B1 * | 3/2001 | Camodeca et al. | 128/207.14 |
| 6,578,574 | B1 * | 6/2003 | Køhnke | 128/203.11 |
| 7,219,668 | B2 * | 5/2007 | Flynn | 128/205.13 |
| 2001/0054423 | A1 * | 12/2001 | Gray | 128/205.13 |
| 2003/0024533 | A1 * | 2/2003 | Sniadach | A61M 16/06 128/205.25 |
| 2005/0139220 | A1 * | 6/2005 | Christopher | 128/207.14 |
| 2005/0235998 | A1 * | 10/2005 | Tresnak et al. | 128/207.14 |

(Continued)

*Primary Examiner* — Bradley Philips
*Assistant Examiner* — Eric Bryant

(57) ABSTRACT

A flexible transparent multiple use face mask that encloses a user's face allowing the user's airway to be ventilated that includes a transparent flexible airway mask that encloses and ventilates a user's airway, an airway adaptor that directs a quantity of ventilation to the transparent flexible airway mask, a manual resuscitation bag valve that receives the airway adaptor and controls the quantity of ventilation directed to the transparent flexible airway mask and a manual resuscitation bag that produces the quantity of ventilation transmitted through the airway adaptor to the transparent flexible airway mask. The multiple-use airway mask can also be turned inside out and be used in combination with an endotracheal tube or a tracheotomy tube and also includes an attachment strap to prevent losing the transparent flexible airway mask as an added safety measure to keep the mask and bag connected.

26 Claims, 5 Drawing Sheets

(56) References Cited

U.S. PATENT DOCUMENTS

2007/0215158 A1\* 9/2007 Kroupa ............. A61M 16/0078
  128/205.13
2007/0261698 A1\* 11/2007 Palatnik ................... 128/207.14
2008/0087285 A1\* 4/2008 Kuo .................. A61M 16/0078
  128/205.13
2010/0095965 A1\* 4/2010 Piper ........................ 128/205.24
2011/0247624 A1\* 10/2011 Von Hollen ............. 128/205.23

\* cited by examiner

MULTIPLE-USE AIRWAY MASK

This application claims priority to U.S. Provisional Application 61/561,617 filed on Nov. 18, 2011, the entire disclosure of which is incorporated by reference.

TECHNICAL FIELD & BACKGROUND

The present invention generally relates to an airway mask. More specifically, the invention is a multiple-use airway mask.

It is an object of the invention to provide a multiple-use airway mask that can be utilized in combination with or without an artificial airway such as an endotracheal tube or a tracheotomy tube.

It is an object of the invention to provide a multiple-use airway mask that can be inverted and can be utilized in a normal position and an inverted position.

It is an object of the invention to provide a multiple-use airway mask that is a single-piece to prevent losing a detachable airway mask.

What is really needed is a multiple-use airway mask that can be utilized in combination with or without an artificial airway such as an endotracheal tube or a tracheotomy tube that can be inverted and can be utilized in a normal position and an inverted position that is a single-piece to prevent losing a detachable airway mask.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1A:
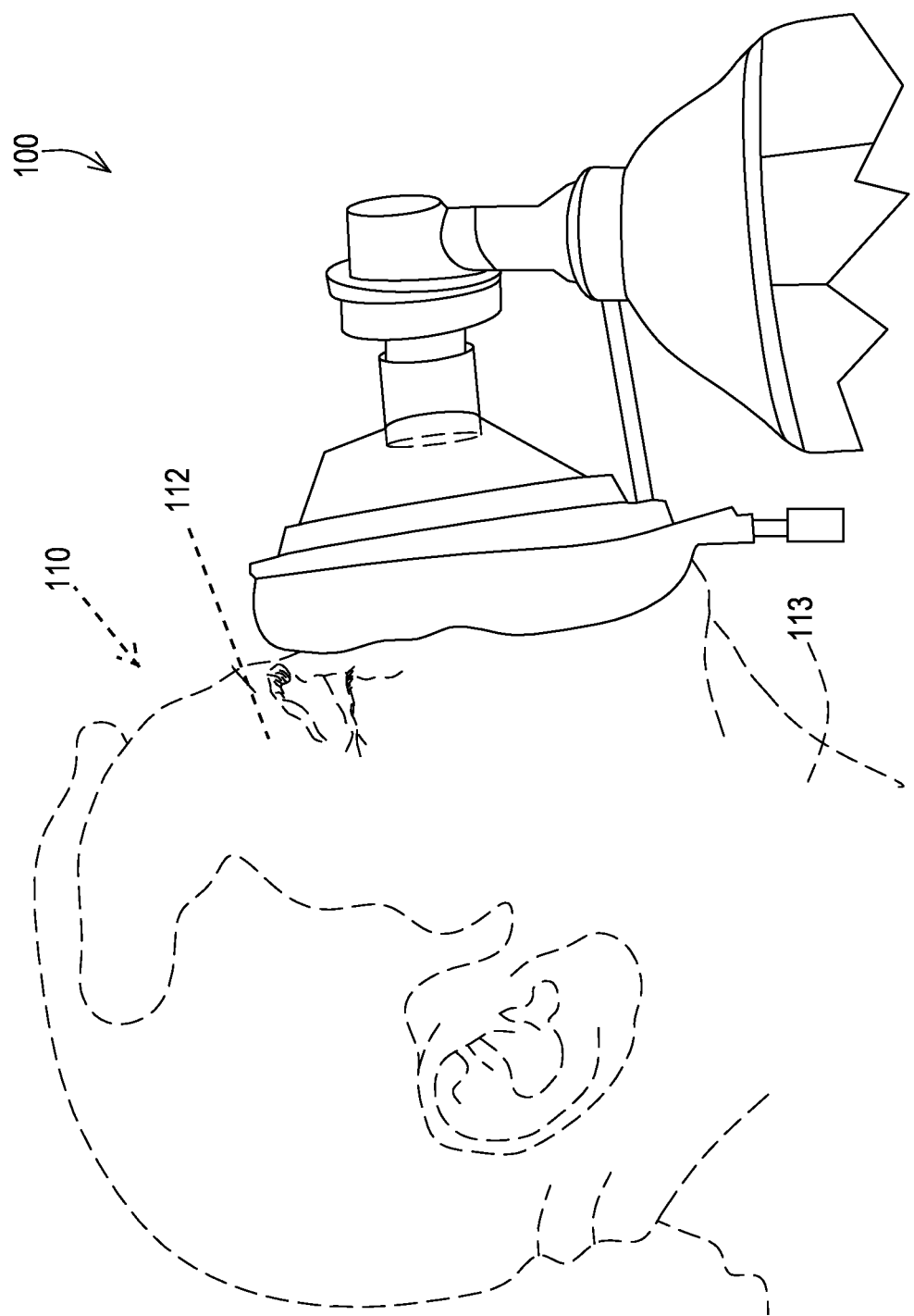
FIG. 1A illustrates a side environmental perspective view of a multiple-use airway mask, in accordance with one embodiment of the present invention.

FIG. 1A illustrates a side environmental perspective view of a multiple-use airway mask 100, in accordance with one embodiment of the present invention.

The multiple-use airway mask 100 illustrated in FIG. 1A includes the multiple-use airway mask 100 and a user 110. The multiple-use airway mask 100 is ventilating the user 110 without the utilization of an artificial airway such as an endotracheal tube (FIG. 2A, 210) or a tracheotomy tube (FIG. 2B, 260). The user 110 is simply placing the multiple-use airway mask 100 against a user's face 112 to ventilate the user 110. Additional details regarding the multiple-use airway mask 100 are illustrated in FIG. 1B.

Figure 1B:
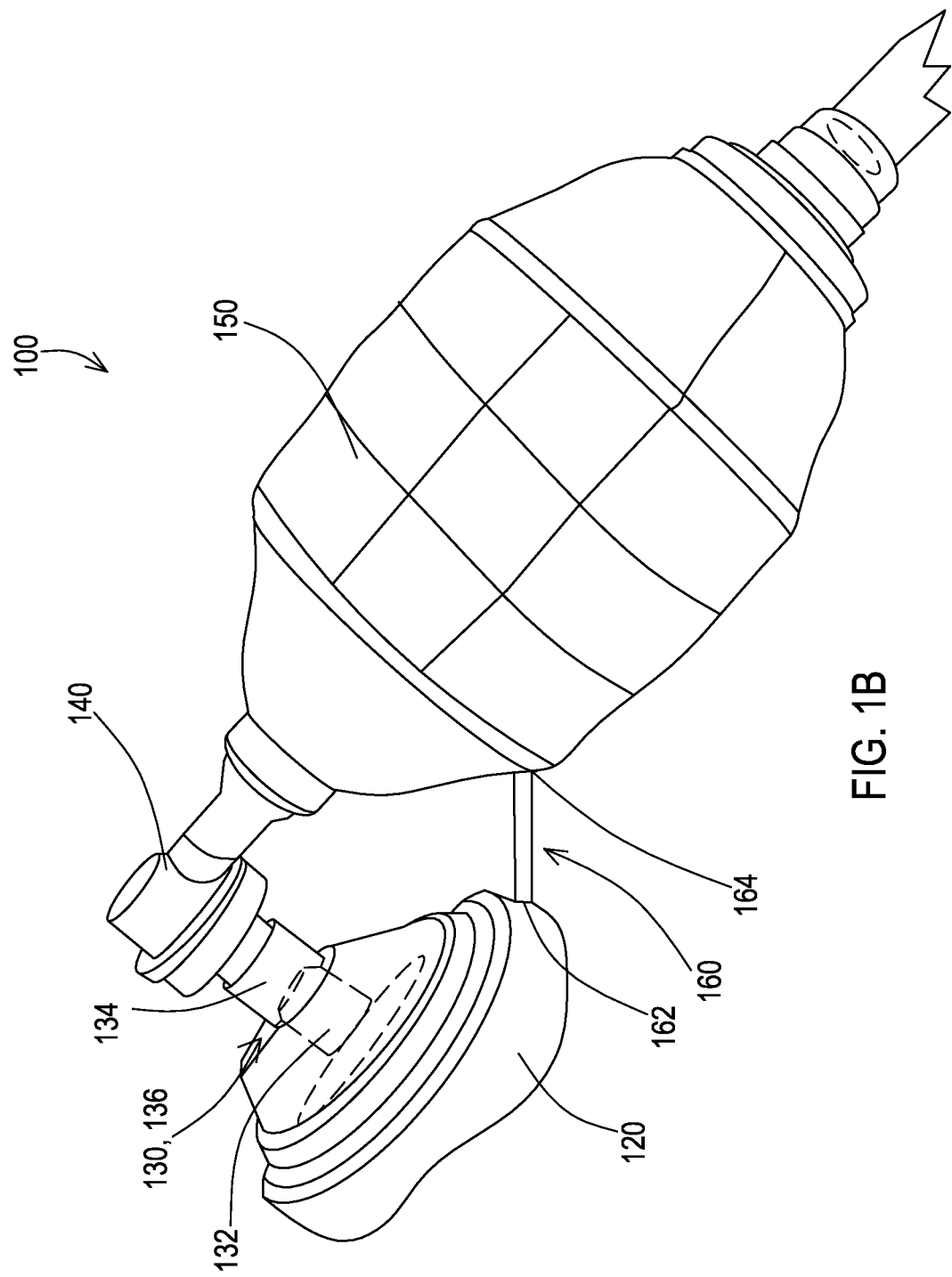
FIG. 1B illustrates a side perspective view of a multiple-use airway mask, in accordance with one embodiment of the present invention.

FIG. 1B illustrates a side perspective view of a multiple-use airway mask 100, in accordance with one embodiment of the present invention. The multiple-use airway mask 100 illustrated in FIG. 1B is similar to the multiple-use airway mask 100 illustrated in FIG. 1A.

The multiple-use airway mask 100 includes a transparent flexible airway mask 120, an airway adaptor 130, a manual resuscitation bag valve 140, a manual resuscitation bag 150 and an attachment strap 160. The transparent flexible airway mask 120 encloses a user's face 112 while the user's airway 113 is ventilated (See FIG. 1A). The transparent flexible airway mask 120 can be enclosed against and removed from the user's face 112 as needed. The transparent flexible airway mask 120 is transparent and allows a health care worker to unobstructedly look over the transparent flexible airway mask 120 to prevent the user 110 from aspirating on secretions and the user 110 is receiving an appropriate air flow or ventilation airway mask. The term unobstructedly is defined as allowing the user 110 to look over the transparent flexible airway mask 120 without the transparent flexible airway mask 120 blocking any user 110 visual capability. The airway adaptor 130 has a first end 132, a second end 134 and has a hollow elongated shape 136. The airway adaptor 130 directs a quantity of ventilation to the transparent flexible airway mask 120. The first end 132 of the airway adaptor 130 has an approximate 15 mm diameter and the second end 134 of the airway adaptor 130 has an approximate 22 mm diameter, although the first end 132 and the second end 134 of the airway adaptor 130 can have any suitable diameter. The first end 132 of the airway adaptor 130 extends inside the transparent flexible airway mask 120 and the second end 134 of the airway adaptor 130 extends outside the transparent flexible airway mask 120. The airway adaptor 130 is permanently bonded to the transparent flexible airway mask 120. The manual resuscitation bag valve 140 receives the second end 134 of the airway adaptor 130 and is permanently bonded to the second end 134 of the airway adaptor 130. The manual resuscitation bag valve 140 controls a quantity of ventilation directed to the transparent flexible airway mask 120. The manual resuscitation bag 150 is permanently attached to the manual resuscitation bag valve 140 and produces a quantity of ventilation transmitted through the airway adaptor 130 to the transparent flexible airway mask 120. The manual resuscitation bag 150 produces a quantity of ventilation by a person, typically a caregiver or a healthcare provider such as a respiratory therapist, a nurse, a doctor, a paramedic or any other suitable person by squeezing the manual resuscitation bag 150. The attachment strap 160 has a first end 162 and a second end 164. The attachment strap 160 keeps the transparent flexible airway mask 120 attached to the manual resuscitation bag 150 as a safety measure due to any malfunction which separates the transparent flexible airway mask 120 from the multiple-use airway mask 100, the transparent flexible airway mask 120 will still be attached or bonded and available. The first end 162 of the attachment strap 160 is attached to the transparent flexible airway mask 120 and the second end 164 of the attachment strap 160 is attached to the manual resuscitation bag 150.

Figure 2A:
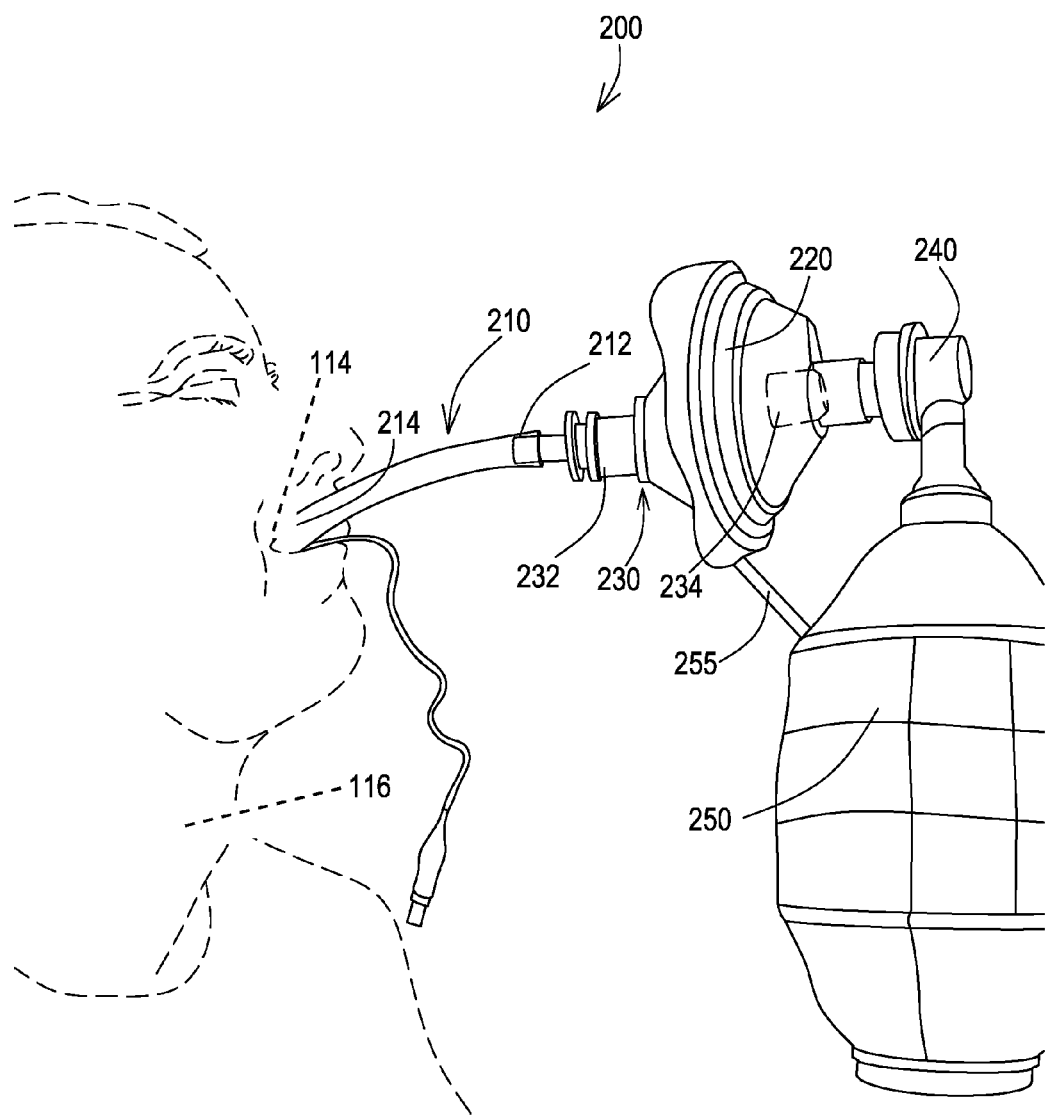
FIG. 2A illustrates a side environmental perspective view of an inverted multiple-use airway mask used in combination with an endotracheal tube, in accordance with one embodiment of the present invention.
Figure 2B:
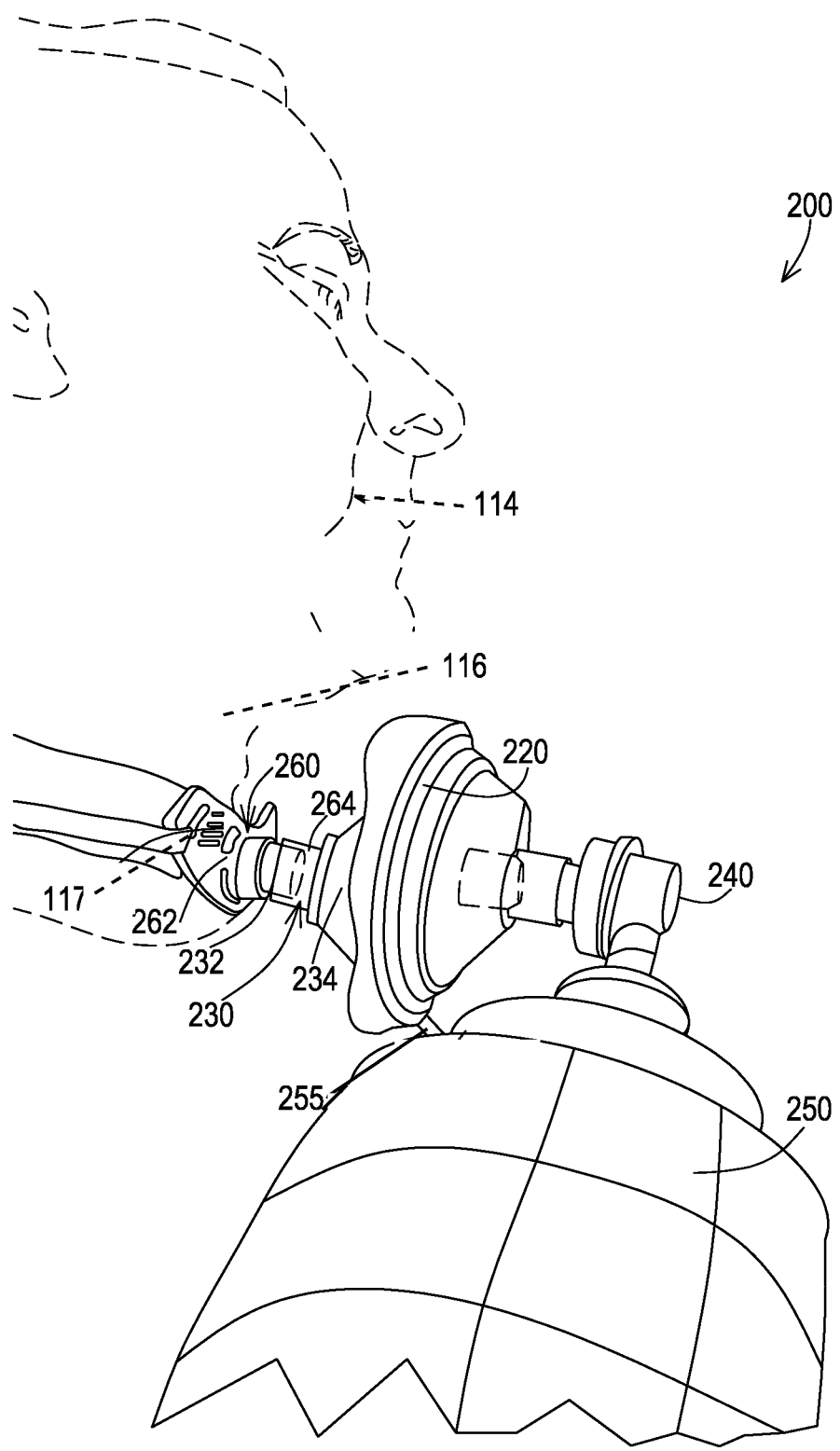
FIG. 2B illustrates a side environmental perspective view of an inverted multiple-use airway mask used in combination with a tracheotomy tube, in accordance with one embodiment of the present invention.

FIG. 2A illustrates a side environmental perspective view of an inverted multiple-use airway mask 200 used in combination with an endotracheal tube 210, in accordance with one embodiment of the present invention. The multiple-use airway mask 200 illustrated in FIG. 2A includes a transparent flexible airway mask 220, an airway adaptor 230, a manual resuscitation bag valve 240, a manual resuscitation bag 250 and an attachment strap 255 that is similar to the multiple-use airway mask 100, the transparent flexible airway mask 120, the airway adaptor 130, the manual resuscitation bag valve 140, the manual resuscitation bag 150 and the attachment strap 160 illustrated in FIG. 1B.

Additionally the multiple-use airway mask 200 includes an endotracheal tube 210. In contrast to FIG. 1B, the transparent flexible airway mask 220 is turned inside-out thereby exposing a first end 232 of the airway adaptor 230 that is similar to the first end 132 of the airway adaptor 130 illustrated in FIG. 1B. The endotracheal tube 210 has a first end 212 and a second end 214 and provides an artificial airway into a user's mouth 114 or a user's airway 116. The first end 212 of the endotracheal tube 210 is removably inserted into the first end 232 of the airway adaptor 230. The second end 214 of the endotracheal tube 210 is removably inserted into the user's mouth 114 or the user's airway 116 to provide a quantity of ventilation to the user's mouth 114 or the user's airway 116. The term removably inserted is defined as allowing an object being inserted into something, such as a user's mouth 114 or a user's airway 116 and being capable of being removed.

FIG. 2B illustrates a side environmental perspective view of an inverted multiple-use airway mask 200 used in combination with a tracheotomy tube 260, in accordance with one embodiment of the present invention. The multiple-use airway mask 200 illustrated in FIG. 2B includes a transparent flexible airway mask 220, an airway adaptor 230, a manual resuscitation bag valve 240 and a manual resuscitation bag 250 that is similar to the multiple-use airway mask 200, the transparent flexible airway mask 220, the airway adaptor 230, the manual resuscitation bag valve 240, the manual resuscitation bag 250 and the attachment strap 255 illustrated in FIG. 2B.

In contrast to FIG. 1B, the transparent flexible airway mask 220 is turned inside-out thereby exposing a first end 232 of the airway adaptor 230 that is similar to the first end 132 of the airway adaptor 130 illustrated in FIG. 1B. The tracheotomy tube 260 has a first end 262 and a second end 264 and provides an artificial airway to a user's airway 116. The first end 262 of the tracheotomy tube 260 is removably inserted into the first end 232 of the airway adaptor 230. The second end 264 of the tracheotomy tube 260 is removably inserted into an aperture 117 on the user's airway 116 to provide a quantity of ventilation to the user's airway 116. The term removably inserted is defined as allowing an object being inserted into something such as a user's mouth 114 or a user's airway 116 and being capable of being removed as previously defined in FIG. 2A.

Figure 2C:
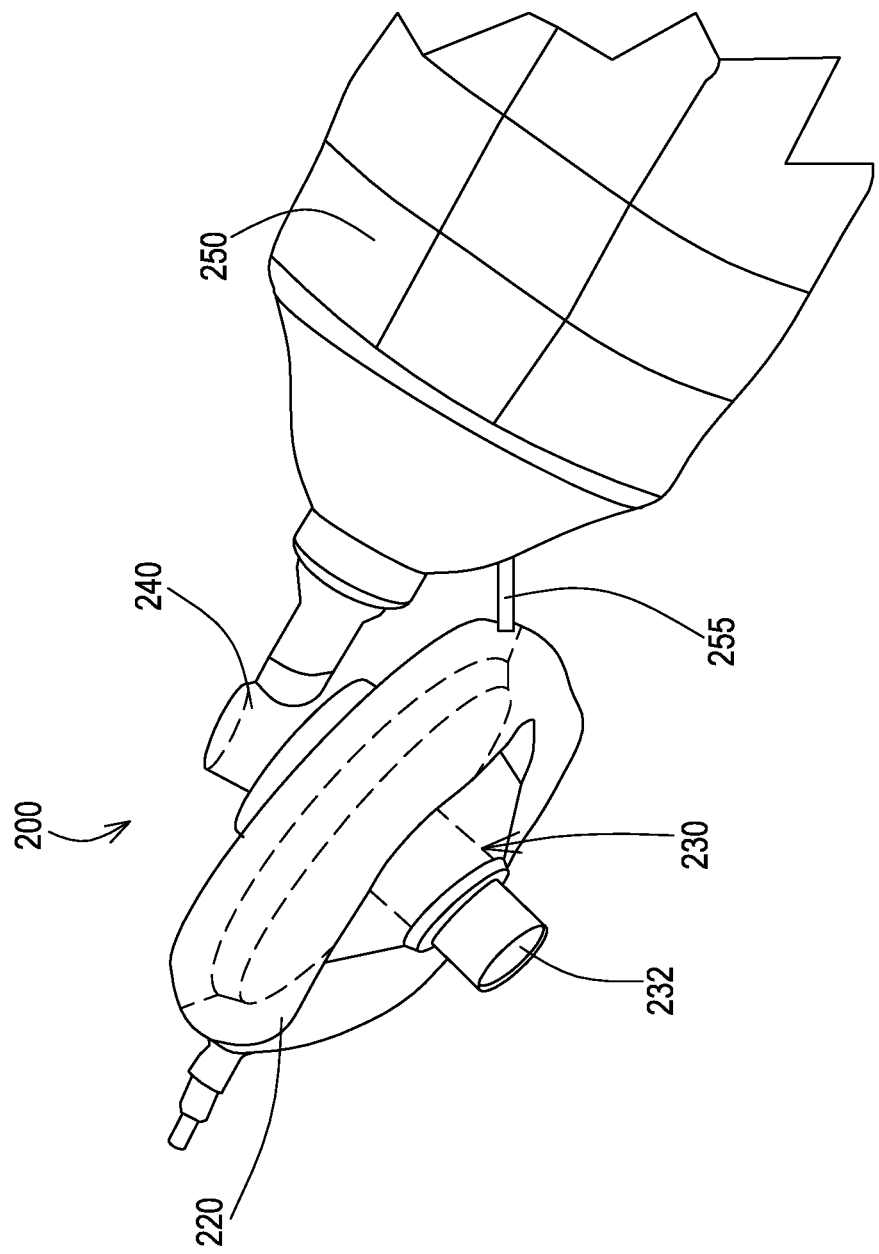
FIG. 2C illustrates a side perspective view of an inverted multiple-use airway mask, in accordance with one embodiment of the present invention.

FIG. 2C illustrates a side perspective view of an inverted multiple-use airway mask 200, in accordance with one embodiment of the present invention.

The multiple-use airway mask 200 illustrated in FIG. 2C includes a transparent flexible airway mask 220, an airway adaptor 230, a manual resuscitation bag valve 240, a manual resuscitation bag 250 and an attachment strap 255 that is similar to the multiple-use airway mask 200, the transparent flexible airway mask 220, the airway adaptor 230, the manual resuscitation bag valve 240, the manual resuscitation bag 250 and the attachment strap 255 illustrated in FIG. 2A and FIG. 2B. The multiple-use airway mask 200 illustrated in FIG. 2C can also be turned inside out to accommodate the endotracheal tube 210 or the tracheotomy tube 260 with the first end 232 of the airway adaptor 230 as illustrated in FIG. 2A and FIG. 2B.

The multiple-use airway mask solves the problem of losing a detachable airway mask. The multiple-use airway mask has no detachable parts and solves the problem of losing an airway mask. The multiple-use airway mask, which can be turned inside-out, is an improvement over a traditional airway mask. The multiple-use airway mask works by ventilating a user with or without an artificial airway. The multiple-use airway mask includes a fixed air adapter that is bonded to the airway mask near the base of the mask between the airway mask and the bag reservoir. The multiple-use airway mask manually ventilates a user with a healthcare provider squeezing the reservoir bag to desired lung inflation. The multiple-use airway mask can be turned inside-out exposing the adapter to accommodate an artificial airway for the purpose of manual ventilation.

The multiple-use airway mask is used to ventilate a user without having to disassemble or reassemble a bag valve mask. The multiple-use airway mask will ventilate a user with or without an artificial airway in any user population. Our design has no detachable parts which will insure that in an event of an unplanned extubation, there will be no loss of an airway mask and will also ensure a quantity of ventilation without a lapse in time, which would put the user at risk for anoxic brain injury or even death from respiratory failure.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A single-piece multiple-use airway mask, comprising:
   a transparent flexible airway mask that encloses a user's face while a user's airway is ventilated, the transparent flexible airway mask allows a health care worker to unobstructedly look over the transparent flexible airway mask to adjust a selected one of an aspiration and an impediment that affect the transparent flexible airway mask, the single-piece multiple-use airway mask prevents losing the transparent flexible airway mask, the transparent flexible airway mask will not detach from the single-piece multiple-use airway mask and become lost from the single-piece multiple-use airway mask because an airway adaptor is permanently bonded to the transparent flexible airway mask, the airway adaptor is permanently bonded to a manual resuscitation bag valve, the manual bag valve is permanently bonded to a manual resuscitation bag making the single-piece multiple-use airway mask single piece;

the airway adaptor has a first end, a second end and a hollow elongated shape, the airway adaptor directs a quantity of ventilation to the transparent flexible airway mask, the airway adaptor is permanently bonded to the transparent flexible airway mask, the first end of the airway adaptor extends inside the transparent flexible airway mask and the second end of the airway adaptor extends outside the transparent flexible airway mask;

the manual resuscitation bag valve receives the second end of the airway adaptor, the manual resuscitation bag valve controls the quantity of ventilation directed to the transparent flexible airway mask;

the manual resuscitation bag is permanently attached to the manual resuscitation bag valve, the manual resuscitation bag produces the quantity of ventilation transmitted through the airway adaptor to the transparent flexible airway mask, the manual resuscitation bag is permanently bonded to the second end of the airway adaptor, the transparent flexible airway mask is provided to be turned inside-out to expose the first end of the airway adaptor to ventilate an artificial airway; and an attachment strap with a first end and a second end, the attachment strap keeps the transparent flexible airway mask attached to the manual resuscitation bag, the first end of the attachment strap is attached to the transparent flexible airway mask and the second end of the attachment strap is attached to the manual resuscitation bag.

2. The multiple-use airway mask according to claim 1, wherein the first end of the airway adaptor has a 15 mm diameter.

3. The multiple-use airway mask according to claim 1, wherein the first end of the airway adaptor has a 22 mm diameter.

4. The multiple-use airway mask according to claim 1, wherein the manual resuscitation bag produces the quantity of ventilation by a selected one of a caregiver and a health care provider.

5. The multiple-use airway mask according to claim 4, wherein the health care provider is a selected one of a respiratory therapist, a nurse, a doctor and a paramedic.

6. The multiple-use airway mask according to claim 1, wherein the first end of the airway adaptor has a 15 mm diameter.

7. The multiple-use airway mask according to claim 1, wherein the first end of the airway adaptor has a 22 mm diameter.

8. The multiple-use airway mask according to claim 1, wherein the first end of the airway adaptor has a 15 mm diameter and the second end of the airway adaptor has a 22 mm diameter.

9. The multiple-use airway mask according to claim 1, wherein the transparent flexible airway mask inverts to ventilate the artificial airway and reverts back to ventilate a user's airway.

10. The multiple-use airway mask according to claim 1, wherein the transparent flexible airway mask ventilates an artificial airway without having to remove the transparent flexible airway mask from the manual resuscitation bag.

11. A single-piece multiple-use airway mask used in combination with an endotracheal tube, comprising:

a transparent flexible airway mask, the single-piece multiple-use airway mask prevents losing the transparent flexible airway mask, the transparent flexible airway mask will not detach from the single-piece multiple-use airway mask and become lost from the single-piece multiple-use airway mask because an airway adaptor is permanently bonded to the transparent flexible airway mask, the airway adaptor is permanently bonded to a manual resuscitation bag valve and the manual bag valve is permanently bonded to a manual resuscitation bag;

the airway adaptor with a first end, a second end and a hollow elongated shape, the airway adaptor directs a quantity of ventilation to the transparent flexible airway mask, the airway adaptor is permanently bonded to the transparent flexible airway mask, the first end of the airway adaptor extends inside the transparent flexible airway mask and the second end of the airway adaptor extends outside the transparent flexible airway mask, the transparent flexible airway mask is turned inside-out exposing the first end of the airway adaptor, the first end of the airway adaptor is releasably attached to the endotracheal tube;

the manual resuscitation bag valve receives the second end of the airway adaptor, the manual resuscitation bag valve controls the quantity of ventilation directed to the transparent flexible airway mask;

the manual resuscitation bag is permanently attached to the manual resuscitation bag valve, the manual resuscitation bag produces a quantity of ventilation transmitted through the airway adaptor to the transparent flexible airway mask, the manual resuscitation bag is permanently bonded to the second end of the airway adaptor; and an attachment strap with a first end and a second end, the attachment strap keeps the transparent flexible airway mask attached to the manual resuscitation bag.

12. The multiple-use airway mask according to claim 11, wherein the manual resuscitation bag produces the quantity of ventilation by a selected one of a caregiver and a health care provider.

13. The multiple-use airway mask according to claim 12, wherein the health care provider is a selected one of a respiratory therapist, a nurse, a doctor and a paramedic.

14. The multiple-use airway mask according to claim 11, wherein the endotracheal tube has a first end and a second end, the endotracheal tube provides an artificial airway into a selected one of a user's mouth and a user's airway.

15. The multiple-use airway mask according to claim 14, wherein the first end of the endotracheal tube is removably inserted into the first end of the airway adaptor.

16. The multiple-use airway mask according to claim 14, wherein the second end of the endotracheal tube is removably inserted into an aperture of the user's airway to provide the quantity of ventilation to the selected one of a user's mouth and the user's airway.

17. The multiple-use airway mask according to claim 11, wherein the transparent flexible airway mask inverts to ventilate the artificial airway and reverts back to ventilate a user's airway.

18. The multiple-use airway mask according to claim 11, wherein the transparent flexible airway mask ventilates an artificial airway without having to remove the transparent flexible airway mask from the manual resuscitation bag.

19. A single-piece multiple-use airway mask used in combination with a tracheotomy tube, comprising:
- a transparent flexible airway mask, the single-piece multiple-use airway mask prevents losing the transparent flexible airway mask, the transparent flexible airway mask will not detach from the single-piece multiple-use airway mask and become lost from the single-piece multiple-use airway mask because an airway adaptor is permanently bonded to the transparent flexible airway mask, the airway adaptor is permanently bonded to a manual resuscitation bag valve, the manual bag valve is permanently bonded to a manual resuscitation bag;
- the airway adaptor with a first end, a second end and a hollow elongated shape, the airway adaptor directs a quantity of ventilation to the transparent flexible airway mask, the airway adaptor is permanently bonded to the transparent flexible airway mask, the first end of the airway adaptor extends inside the transparent flexible airway mask and the second end of the airway adaptor extends outside the transparent flexible airway mask, the transparent flexible airway mask is turned inside-out exposing the first end of the airway adaptor and the first end of the airway adaptor is releasably attached to the tracheotomy tube;
- the manual resuscitation bag valve receives the second end of the airway adaptor, the manual resuscitation bag valve controls the quantity of ventilation directed to the transparent flexible airway mask; and
- the manual resuscitation bag is permanently attached to the manual resuscitation bag valve, the manual resuscitation bag produces the quantity of ventilation transmitted through the airway adaptor that is permanently bonded to the transparent flexible airway mask, the manual resuscitation bag is permanently bonded to the second end of the airway adaptor; and
- an attachment strap with a first end and a second end, the attachment strap keeps the transparent flexible airway mask attached to the manual resuscitation bag.

20. The multiple-use airway mask according to claim 19, wherein the manual resuscitation bag produces the quantity of ventilation by a selected one of a caregiver and a health care provider.

21. The multiple-use airway mask according to claim 20, wherein the health care provider is a selected one of a respiratory therapist, a nurse, a doctor and a paramedic.

22. The multiple-use airway mask according to claim 19, wherein the tracheotomy tube has a first end and a second end, the tracheotomy tube provides an artificial airway into an aperture of a user's airway.

23. The multiple-use airway mask according to claim 22, wherein the first end of the tracheotomy tube is removably inserted into the first end of the airway adaptor.

24. The multiple-use airway mask according to claim 22, wherein the second end of the tracheotomy tube is removably inserted into the aperture of the user's airway to provide the quantity of ventilation to the aperture of the user's airway.

25. The multiple-use airway mask according to claim 19, wherein the transparent flexible airway mask inverts to ventilate the artificial airway and reverts back to ventilate a user's airway.

26. The multiple-use airway mask according to claim 19, wherein the transparent flexible airway mask ventilates an artificial airway without having to remove the transparent flexible airway mask from the manual resuscitation bag.

* * * * *